United States Patent [19]

Pohl et al.

[11] Patent Number: 5,259,915

[45] Date of Patent: Nov. 9, 1993

[54] ORGANOMETALLIC COMPOUNDS

[75] Inventors: Ludwig Pohl, Darmstadt; Herbert Schumann, Berlin; Wilfried Wassermann, Berlin; Uwe Hartmann, Berlin; Thomas Seuss, Berlin, all of Fed. Rep. of Germany

[73] Assignee: Merck Patent Gesellschaft Beschränkter Haftung, Darmstadt, Fed. Rep. of Germany

[21] Appl. No.: 856,795

[22] Filed: Mar. 24, 1992

[30] Foreign Application Priority Data

Mar. 25, 1991 [DE] Fed. Rep. of Germany ....... 4109723

[51] Int. Cl.$^5$ ............................................. C36B 19/00
[52] U.S. Cl. ................................... 156/600; 156/610; 156/622; 156/624; 156/DIG. 72; 156/DIG. 113
[58] Field of Search ............... 156/610, 600, 613, 614, 156/622, 624, DIG. 72, DIG. 113; 437/85, 86; 564/534

[56] References Cited

PUBLICATIONS

Atwood et al, "Cationic Aluminum Hydrides: B-N,N,N',N'',N''-pentamethyldiethyleneamine...", J. Chem. Soc., Chem. Commun. (23) 1697-1699 1991.
Bradley et al., "The Volatilities of Some Adducts of Trimethylindium", Jour. Crystal Growth, 92(1988) pp. 37 to 45.

*Primary Examiner*—Robert Kunemund
*Attorney, Agent, or Firm*—Millen, White, Zelano, & Branigan

[57] ABSTRACT

The invention relates to organometallic compounds of the elements aluminum, gallium and indium which are two-fold intramolecularly stabilized, and to the use thereof for the production of thin films and epitaxial layers by deposition from the liquid or solid phase.

18 Claims, No Drawings

ORGANOMETALLIC COMPOUNDS

SUMMARY OF THE INVENTION

The invention relates to organometallic compounds which contain aluminum, gallium or indium as metals, and to the use of these compounds for the production of thin films or epitaxial layers by deposition of the metal, principally from the liquid or solid phase, with decomposition of the organometallic compound.

The deposition of such layers of either pure elements from the third group or of combinations with other elements, such as, for example, gallium arsenide, indium phosphide or gallium phosphide, can be used for the production of electrical, electronic, optical or optoelectronic switching elements, compound semiconductors and lasers.

The properties of these films depend on the deposition conditions and on the chemical composition of the deposited film.

The deposition of these layers can take place from the solid phase, the liquid phase or the gas phase.

Deposition from the gas phase can be carried out by any known method, such as the metal-organic chemical vapor deposition (MOCVD) method, the photo-metal-organic vapor phase (photo-MOVP) method, the laser-chemical vapor deposition (laser-CVD) method or the metal-organic magnetron scattering (MOMS) method.

In the MOCVD method, organometallic compounds are employed which decompose at a temperature below about 1100° C. with deposition of the metal. Typical apparatuses currently used for MOCVD comprise a "bubbler" having an inlet for the organometallic component, a reaction chamber which contains the substrate to be coated, and a source for a carrier gas, which should be inert toward the organometallic component. The bubbler is kept at a constant, relatively low temperature, which is preferably above the melting point of the organometallic compound, but well below the decomposition temperature. The reaction or decomposition chamber preferably has a much higher temperature, but below 1100° C., at which the organometallic compound decomposes fully and the metal is deposited. Due to the carrier gas, the organometallic compound is converted into the vapor state and flushed into the decomposition chamber with the carrier gas. The mass flow of the vapor here can be controlled precisely, and controlled growth of the thin layers is thus also possible.

The other methods of gas-phase deposition differ from this essentially only through the way in which the energy required for the decomposition is supplied.

The gas-phase deposition methods have the disadvantage that they are complex from a technical and equipment point of view and that they require complex control and monitoring of numerous process parameters.

In this respect, processes for deposition from the liquid or solid phase are significantly more favorable. Here, it is only necessary to provide the substrate with a liquid or solid coating containing a suitable organometallic compound and then to treat it, for example thermally, in order to decompose the organometallic compound.

Hitherto, epitaxial layers have been produced principally using alkylmetal compounds, such as, for example, trimethylgallium, trimethylaluminum or trimethylindium. These very volatile compounds are extremely sensitive to air and moisture, are spontaneously combustible and in some cases decompose even at room temperature. Complex safety precautions are therefore necessary for the preparation, transport, storage and use of these compounds. Their high volatility alone means that these alkylmetal compounds can only be employed in gas-phase deposition methods. A high loss of unreacted alkylmetal compound is unavoidable in gas-phase epitaxy for system-related reasons. Due to the sensitivity, disposal is difficult and recovery virtually impossible.

Stabilized alkylmetal compounds which have been disclosed in the meantime, such as, for example, adducts with Lewis bases, such as, for example, trimethylamine and triphenylphosphine (for example, described in GB 2,123,422, Ep-A 108 469 or EP-A 176 537), or intramolecularly stabilized compounds of this type (for example, described in DE-A 36 31 469 and DE-A 38 41 643) can likewise only be employed in gas-phase deposition methods due either to still inadequate stability or to high volatility.

An object of the present invention was to find alkylmetal compounds which are insensitive and simple to handle and which are suitable for deposition of the metal from the liquid or solid phase.

Upon further study of the specification and appended claims, further objects and advantages of this invention will become apparent to those skilled in the art.

It has now been found that organometallic compounds of formula I

in which
M is aluminum, gallium or indium,
X is —CH, N or a 5- or 6-membered aromatic, heterocyclic or cycloaliphatic ring, in each case substituted by Y in the o,o'-position,
Y is —(CH$_2$)$_n$—NR$^3$R$^4$, —(CH$_2$)$_n$—PR$^3$R$^4$, —(CH$_2$)$_n$—AsR$^3$R$^4$ or —(CH$_2$)$_n$—SbR$^3$R$^4$ where n is 1, 2 or 3, and
R$^1$, R$^2$, R$^3$ and R$^4$ are each, independently of one another, hydrogen or an alkyl having 1 to 8 carbon atoms which may be partially or completely fluorinated,
satisfy said conditions in an excellent manner.

The novel compounds of formula I are two-fold intramolecularly stabilized by electron transfer from the nitrogen, phosphorus, arsenic or antimony atom of the group Y to the electron-deficient IIIa element, i.e., M. They therefore have particularly high stability towards air and oxygen. They are very simple to handle since they are not spontaneously combustible and do not decompose even at room temperature. However, they decompose with deposition of the metal on heating to about 1100°. It has been shown that the compounds of the formula I have a low vapor pressure and thus only low volatility. They are therefore particularly suitable for deposition of the metal from the liquid or solid phase. Since the compounds of the formula I contain stable and readily removable leaving groups, low incorporation of carbon results, which has great advantages for the quality of the end products.

The invention thus relates to the organometallic compounds of the formula I.

The invention also relates to the use of the organometallic compounds of the formula I for deposition of the metal onto substrates, in particular from the liquid or solid phase.

The invention furthermore relates to a process for the production of layers on substrates by deposition of the metal from organometallic compounds in which a liquid or solid coating containing an organometallic compound of the formula I is produced on the substrate and subsequently heated to above the decomposition temperature.

In the formula I, M is aluminum (Al), gallium (Ga) or indium (In), preferably Ga or In.

X is a CH group which is in each case substituted by two groups Y, corresponding substituted N, or a 5- or 6-membered aromatic, heterocyclic or cycloaliphatic ring which is in each case substituted by two radicals Y in the o,o'-position. Heterocyclic rings preferably contain up to three hetero atoms, i.e., N, S and/or O atoms, with N being preferred. Possible 5-membered rings are principally cyclopentyl, cyclopentenyl, cyclopentadienyl, pyrrole and pyrrolidine. Possible 6-membered rings are principally phenyl, 4-pyridyl, cyclohexyl, cyclohexenyl and cyclohexadienyl. X is preferably a phenyl ring.

The radicals $R^1$ and $R^2$ bonded to the metal atom M may be hydrogen or alkyl groups having 1-8 carbon atoms, if desired partially or completely fluorinated. $R^1$ and $R^2$ are preferably alkyl groups having 1-4 carbon atoms, in particular methyl, ethyl, n-propyl or isopropyl.

Y is a $-(CH_2)_n-NR^3R^4$, $-(CH_2)_n-PR^3R^4$, $-(CH_2)_n-AsR^3R^4$ or $-(CH_2)_n-SbR^3R^4$ group, in which $R^3$ and $R^4$ may each be desired partially or completely fluorinated, and n is the number 1, 2 or 3. $R^3$ and $R^4$ are preferably alkyl groups having 1-4 carbon atoms, in particular methyl or ethyl. Y is particularly preferably the $-(CH_2)_n-NR^3R^4$ group.

Examples of fluorinated groups for $R^1$, $R^2$, $R^3$ and $R^4$ and $CF_3$ and $C_2F_5$. Such groups are introduced by alkylation with conventional fluorinated compounds as alkylating agents.

The subformulae Ia, Ib and Ic

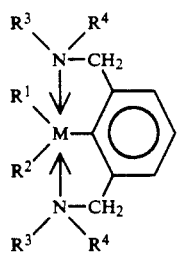 (Ia)

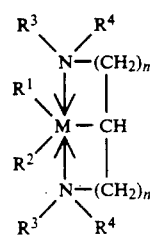 (Ib)

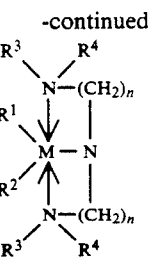 (Ic)

in which M, $R^1$, $R^2$, $R^3$ and $R^4$ are as defined above, are particularly preferred groups of organometallic compounds according to the invention.

In the compounds of the formulae I, Ia, Ib and Ic, the specific arrangement of the groups Y in the o,o'-position of the ring X bonded to the metal atom M or on the group X if the latter is —CH or —N means that in each case two electron-rich atoms of main group V enter, in a sterically particularly favorable manner, the electron-deficient coordination sphere of the metal atom M. This results in particularly effective stabilization of the organometallic compound.

The compounds of the formulae I, Ia, Ib and Ic are prepared by methods known per se, as described in the literature (for example G. Bähr, P. Burbar, Methoden der organischem Chemie [Methods of Organic Chemistry], Volume XIII/4, Georg Thieme Verlag, Stuttgart (1970)), to be precise under reaction conditions which are known and suitable for said reactions. Use may also be made here of variants which are known per se, but are not described here in greater detail.

Thus, compounds of the formulae I, Ia, Ib and Ic can be prepared, for example, by reacting dialkyl chlorides of the elements Al, Ga or In with an organoalkali metal compound whose organic radical is the group $XY_2$, or with a corresponding Grignard compound in an inert solvent. Suitable solvents are all those which do not interfere with the reaction and do not participate in the reaction proceedings. The reaction temperatures essentially correspond to those known from the literature for the preparation of similar compounds.

The organometallic compounds of the formulae I, Ia, Ib and Ic according to the invention prove to be acceptably stable towards air, atmospheric moisture and oxygen. They do not undergo any change, even when exposed to air for a relatively long period. They are stable at room temperature, but can be decomposed at elevated temperature with deposition of the metal. The compounds of the formula I are predominantly solid at room temperature, having low melting points, usually in the range from 30° to 100° C. In addition, they have low vapor pressure at room temperature, i.e. have only low volatility. Their solubility in organic solvents, such as, for example, aliphatic or aromatic hydrocarbons or ethers, is excellent.

Due to these properties, the organometallic compounds of the formula I are fundamentally suitable for all methods of deposition of metals by decomposition of organometallic compounds.

The organometallic compounds of the formula I are particularly suitable and preferably used for the deposition of the metal from the liquid or solid phase, in particular for liquid-phase epitaxy.

In the process according to the invention for the production of thin films or epitaxial layers on any desired substrates, any method known per se for the deposition from the liquid or solid phase can be used, but the organometallic compounds of the formula I are employed.

Such processes are extremely simple to carry out; technically very complex and, therefore, expensive plants as are common in gas-phase epitaxy are not required.

In accordance with the present invention, an elemental metal layer or a metal compound layer (e.g., a compound of Group III and Group V) can be deposited. For example, a metal layer can be deposited using compounds of formula I wherein Y is $-(CH_2)_n-NR^3R^4$. Metal compound layers can, for example, be obtained using compounds of Formula I wherein Y is $-(CH_2)_n-PR^3R^4$, $-(CH_2)_n-AsR^3R^4$ and $-(CH_2)_n-SbR^3R^4$.

The process according to the invention can be carried out, for example, by coating a substrate, for example, a silicon wafer, with a liquid formulation containing an organometallic compound of the formula I - in the simplest case this is a solution of this compound in an organic solvent. Typical organic solvents are alkanes such as pentane, hexane, heptane and ethers such as diethyl ether. The concentration of the organometallic compound in the liquid formulation depends upon the specific solubility of the respective compounds. A preferred concentration is about 10-25% by weight. The coating can preferably take place by the spin-coating method, which is known per se. In this, a certain amount of the liquid solution of formulation is applied in the center of the substrate, and the latter is then rotated at a preselected speed. A film of uniform thickness forms on the surface of the substrate; the thickness of the film can be adjusted by means of the rotational speed and by means of the viscosity of the formulation and its metal content can be predetermined through the concentration of the organometallic compound. After evaporation of the solvent and heating to above the decomposition temperature of the organometallic compound, the metal layer is obtained on the substrate.

Solid phase or liquid phase deposition depends upon whether the respective compound is in the solid state or liquid state.

For the production of mixed metal layers, compound semiconductors, electrical, electronic, optical and optoelectronic components or semiconductor lasers, the formulation can also contain compounds of different metals and of other elements of the periodic table, preferably compounds of elements from main group V (e.g., P, As, or Sb). It is also possible for one or more compounds which are gaseous under the reaction conditions used, in particular compounds of arsenic, antimony or phosphorus, such as, for example, $AsH_3$, $As(CH_3)_3$, or further dopes to be fed into the gas space of the decomposition chamber, during the decomposition process. Dopes which can be employed are principally volatile organometallic compounds of iron, magnesium, zinc or chromium. Examples of preferred compounds here are $Zn(CH_3)_2$, $Mg(CH_3)_2$ and $Fe(C_5H_5)_2$.

It is furthermore possible to add the compounds of the formula I, themselves as dopes in the deposition processes, to other organometallic compounds.

For system-connected reasons, only about 1-10% of the organometallic compounds employed can be deposited on the substrate as an epitaxy layer in the gas-phase epitaxy and corresponding plants currently used. The degree of utilization of the expensive organometallic compounds is accordingly very low here and recovery, if possible at all, and destruction of the excess of organometallic compounds is difficult.

By contrast, the degree of utilization of the organometallic compounds of the formula I according to the invention in the process of liquid-phase or solid-phase epitaxy is very high and recovery of excess amounts is simple due to the high stability of the compounds according to the invention. The organometallic compound deposited as an epitaxy layer in liquid phase or solid phase epitaxy is generally about 10-75% and can be up to 100%.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius. m.p. denotes melting point and b.p. denotes boiling point. Unless otherwise indicated, all parts and percentages are by weight.

The entire disclosures of all applications, patents and publications, cited above and below, and of corresponding application Federal Republic of German P 41 09 723.8, filed May 25, 1991, are hereby incorporated by reference.

EXAMPLES

Example 1

3.0 mmol of 2,6-bis(dimethylaminomethylene)-phenyllithium, obtained from 0.82 g (3.0 mmol) of 2,6-bis(dimethylaminomethylene)phenyl bromide and 1.9 ml of n-butyllithium (3.0 mmol; 1.6 mol/l in hexane), are added to a solution of 0.4 g (3.0 mmol) of dimethylgallium chloride in 10 ml of hexane. The mixture is stirred at room temperature for 12 hours and filtered, the solvent is stripped off in vacuo, and the residue is sublimed in vacuo, giving [2,6-bis(dimethylaminomethylene)-phenyl]dimethylgallium as colorless crystals, m.p. 34° C.

Example 2

2.71 g (10.0 mmol) of 2,6-bis(dimethylaminomethylene)phenyl bromide in 40 ml of hexane, 6.3 ml of n-butyllithium (10.0 mmol; 1.6 mol/l in hexane) and 1.8 g (10.0 mmol) of dimethylindium chloride in 20 ml of hexane are reacted analogously to Example 1 to give [2,6-bis(di-methylaminomethylene)phenyl] dimethylindium, which is obtained in the form of colorless crystals, m.p. 53° C., by cooling a concentrated hexane solution to −30° C.

Example 3

2.5 g (9.2 mmol) of 2,6-bis(dimethylaminomethylene)-phenyl bromide in 40 ml of hexane, 5.8 ml of n-butyllithium (9.2 mmol; 1.6 mol/l in hexane) and 1.92 g (10.0 mmol) of diethylindium chloride in 20 ml of hexane are reacted analogously to Example 2 to give [2,6-bis(dimethylaminomethylene phenyl]diethylindium as colorless crystals, m.p. 41° C.

Example 4

2.2 g (8.1 mmol) of 2,6-bis(dimethylaminomethylene)-phenyl bromide in 40 ml of hexane, 5.1 ml of n-butyllithium (8.1 mmol; 1.6 mol/l in hexane) and 1.90 g (8.1 mmol) of di-n-propylindium in 20 ml of hexane are reacted analogously to Example 1 to give [2,6-bis(dimethylaminomethylene)phenyldi-n-propylidium, which is obtained as a colorless liquid, b.p. 125° C./0.03 mbar, by vacuum distillation.

Example 5

2.4 g (7.3 mmol) of 2,6-bis(diethylaminomethylene)-phenyl bromide in 40 ml of hexane, 4.6 ml of butyllithium (7.3 mmol; 1.6 mol/l in hexane) and 1.5 g (7.3 mmol) of diethylindium chloride in 20 ml hexane are reacted analogously to Example 1 to give [2,6-bis(diethylaminomethylene)phenyl]diethylindium, which is obtained as a colorless liquid, b.p. 115° C./0.04 mbar, by vacuum distillation.

The following are obtained analogously:
[2,6-bis(diethylaminomethylene)phenyl]di-n-propylindium
[2,6-bis(diethylaminomethylene)phenyl]dimethylindium
[2,6-bis(dimethylaminomethylene)phenyl]diethylgallium
[2,6-bis(dimethylaminomethylene)phenyl]di-n-propylgallium
[2,6-bis(diethylaminomethylene)phenyl]dimethylgallium
[2,6-bis(diethylaminomethylene)phenyl]diethylgallium
[2,6-bis(diethylaminomethylene)phenyl]di-n-propylgallium
[2,6-bis(dimethylaminomethylene)phenyl]dimethylaluminum
[2,6-bis(dimethylaminomethylene)phenyl]diethylaluminum
[2,6-bis(dimethylaminomethylene)phenyl]di-n-propylaluminum
[2,6-bis(diethylaminomethylene)phenyl]dimethylaluminum
[2,6-bis(diethylaminomethylene)phenyl]diethylaluminum
[2,6-bis(diethylaminomethylene)phenyl]di-n-propylaluminum
[3-(1,5-dimethylamino)pentyl]dimethylgallium
[3-(1,5-dimethylamino)pentyl]diethylgallium
[3-(1,5-dimethylamino)pentyl]di-n-propylgallium
[3-(1.5-diethylamino)pentyl]dimethylgallium
[3-(1,5-diethylamino)pentyl]diethylgallium
[3-(1,5-diethylamino)pentyl]di-n-propylgallium
[3-(1,5-dimethylamino)pentyl]dimethylindium
[3-(1,5-dimethylamino)pentyl]diethylindium
[3-(1,5-dimethylamino)pentyl]di-n-propylindium
[3-(1,5-diethylamino)pentyl]dimethylindium
[3-(1,5-diethylamino)pentyl]diethylindium
[3-(1,5-diethylamino)pentyl]di-n-propylindium
[3-(1,5-dimethylamino)pentyl]dimethylaluminum
[3-(1,5-dimethylamino)pentyl]diethylaluminum
[3-(1,5-dimethylamino)pentyl]di-n-propylaluminum
[3-(1,5-diethylamino)pentyl]dimethylaluminum
[3-(1,5-diethylamino)pentyl]diethylaluminum
[3-(1,5-diethylamino)pentyl]di-n-propylaluminum
[4-(1,7-dimethylamino)heptyl]dimethylgallium
[4-(1,7-dimethylamino)heptyl]diethylgallium
[4-(1,7-dimethylamino)heptyl]di-n-propylgallium
[4-(1,7-diethylamino)heptyl]dimethylgallium
[4-(1,7-diethylamino)heptyl]diethylgallium
[4-(1,7-diethylamino)heptyl]di-n-propylgallium
[4-(1,7-dimethylamino)heptyl]dimethylindium
[4-(1,7-dimethylamino)heptyl]diethylindium
[4-(1,7-dimethylamino)heptyl]di-n-propylindium
[4-(1,7-diethylamino)heptyl]dimethylindium
[4-(1,7-diethylamino)heptyl]diethylindium
[4-(1,7-diethylamino)heptyl]di-n-propylindium
[4-1,7-dimethylamino)heptyl]dimethylaluminum
[4-(1,7-dimethylamino)heptyl]diethylaluminum
[4-(1,7-dimethylamino)heptyl]di-n-propylaluminum
[4-(1,7-diethylamino)heptyl]dimethylaluminum
[4-(1,7-diethylamino)heptyl]diethylaluminum
[4-(1,7-diethylamino)heptyl]di-n-propylaluminum
Dimethylgallium [bis(2-dimethylaminoethyl]amide
Diethylgallium [bis(2-dimethylaminoethyl)]amide
Di-n-propylgallium [bis(2-dimethylaminoethyl)]amide
Dimethylgallium [bis(2-diethylaminoethyl)]amide
Diethylgallium [bis(2-diethylaminoethyl)]amide
Di-n-propylgallium [bis(2-diethylaminoethyl)]amide
Dimethylindium [bis(2-dimethylaminoethyl)]amide
Diethylindium [bis(2-dimethylaminoethyl)]amide
Di-n-propylindium [bis(2-dimethylaminoethyl)]amide
Dimethylindium [bis(2-diethylaminoethyl)]amide
Diethylindium [bis(2-diethylaminoethyl)]amide
Di-n-propylindium [bis(2-diethylaminoethyl)]amide
Dimethylaluminum [bis(2-dimethylaminoethyl)]amide
Diethylaluminum [bis(2-dimethylaminoethyl)]amide
Di-n-propylaluminum [bis(2-dimethylaminoethyl)]amide
Dimethylaluminum [bis(2-diethylaminoethyl)]amide
Diethylaluminum [bis(2-diethylaminoethyl)]amide
Di-n-propylaluminum [bis(2-diethylaminoethyl)]amide
Dimethylgallium [bis(2-dimethylaminopropyl)]amide
Diethylgallium [bis(2-dimethylaminopropyl)]amide
Di-n-propylgallium [bis(2-dimethylaminopropyl)]amide
Dimethylgallium [bis(2-diethylaminopropyl)]amide
Diethylgallium [bis(2-diethylaminopropyl)]amide
Di-n propylgallium [bis(2-diethylaminopropyl)]amide
Dimethylindium [bis(2-dimethylaminopropyl)]amide
Diethylindium [bis(2-dimethylaminopropyl)]amide
Di-n-propylindium [bis(2-dimethylaminopropyl)]amide
Dimethylindium [bis(2-diethylaminopropyl)]amide
Diethylindium [bis(2-diethylaminopropyl)]amide
Di-n-propylindium [bis(2-diethylaminopropyl)]amide
Dimethylaluminum [bis(2-dimethylaminopropyl)]amide
Diethylaluminum [bis(2-dimethylaminopropyl)]amide
Di-n-propylaluminum [bis(2-dimethylaminopropyl)]amide
Dimethylaluminum [bis(2-diethylaminopropyl)]amide
Diethylaluminum [bis(2-diethylaminopropyl)]amide
Di-n-propylaluminum [bis(2-diethylaminopropyl)]amide The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a method for depositing a metal on a substrate comprising decomposing a metal-containing compound, wherein said metal is Al, In or Ga and is deposited on said substrate, the improvement comprising said compound being an organometallic compound of formula I

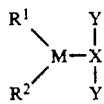

wherein

M is aluminum, gallium or indium;

X is —CH, N or a 5- or 6-membered aromatic, heterocyclic or cycloaliphatic ring, in each case substituted by Y in the o,o'-position;

Y is —(CH$_2$)$_n$—NR$^3$R$^4$, —(CH$_2$)$_n$—PR$^3$R$^4$, —(CH$_2$)$_n$—AsR$^3$R$^4$ or

R$^1$, R$^2$, R$^3$ and R$^4$ are each, independently of one another, hydrogen or an alkyl having 1 to 8 carbon atoms which may be partially or completely fluorinated.

2. A method according to claim 1, wherein said metal is deposited from a liquid or solid phase.

3. A method according to claim 1, wherein deposition of said metal results in the formation of epitaxial layer.

4. A method according to according to claim 1, wherein deposition of said metal results in the production of electrical, electronic, optical and optoelectronic components.

5. A process for the production of a layer on a substrate comprising deposition of metal from an organometallic compound, wherein a liquid or solid coating containing an organometallic compound of the formula I

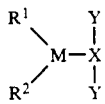

wherein

M is aluminum, gallium or indium;

X is —CH, N or a 5- or 6-membered aromatic, heterocyclic or cycloaliphatic ring, in each case substituted by Y in the o,o'-position;

Y is —(CH$_2$)$_n$—NR$^3$R$^4$, —(CH$_2$)$_n$—PR$^3$R$^4$, —(CH$_2$)$_n$—AsR$^3$R$^4$ or —(CH$_2$)$_n$—SbR$^3$R$^4$ where n is 1, 2 or 3; and R$^1$, R$^2$, R$^3$ and R$^4$ are each, independently of one another, hydrogen or an alkyl having 1 to 8 carbon atoms which may be partially or completely fluorinated, is produced on the substrate and subsequently heated to above the decomposition temperature.

6. A process according to claim 5, wherein the coating containing the organometallic compound of formula I further comprising adding compounds of other elements and/or dopants.

7. A process according to claim 5, wherein the decomposition temperature is about 1100° C.

8. A process according to claim 6, wherein the other elements are selected from compounds of arsenic, antimony or phosphorous.

9. A compound according to claim 6, wherein said dopant is selected from organometallic compounds of iron, magnesium, zinc or chromium.

10. A process according to claim 1, wherein M is gallium or indium.

11. A process according to claim 1, wherein Y is —(CH$_2$)$_n$—NR$^3$R$^4$.

12. A process according to claim 1, wherein X is a phenyl ring.

13. A process according to claim 1 wherein the organometallic compound is formula Ia, Ib or Ic

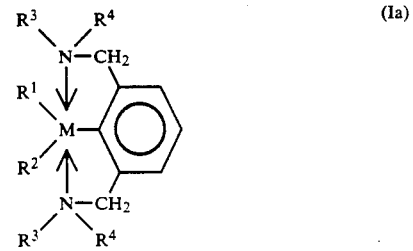

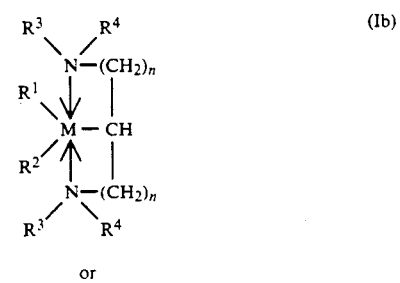

or

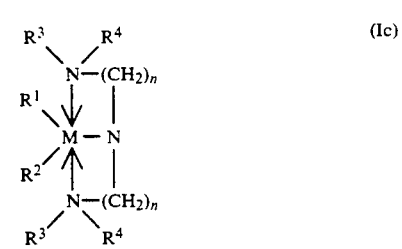

14. A process according to claim 1, wherein n is 1.
15. A process according to claim 1, wherein n is 2.
16. A process according to claim 1, wherein n is 3.
17. A process according to claim 2, wherein R$^1$ and R$^2$ are each independently methyl, ethyl, n-propyl or isopropyl.
18. A process according to claim 1, wherein R$^1$ and R$^2$ are each independently methyl, ethyl, n-propyl or isopropyl.

* * * * *